(12) United States Patent
Burghart et al.

(10) Patent No.: US 6,306,843 B1
(45) Date of Patent: Oct. 23, 2001

(54) METHOD FOR PRODUCING STABLE ACETYLSALICYLIC ACID SOLUTIONS

(76) Inventors: Walter Burghart, Salmgasse 4, A-1030, Vienna (AT); Kurt Burghart, Sägeberg 8, D-22548 Rosdorf (DE)

( * ) Notice: Subject to any disclaimer, the term of this patent is extended or adjusted under 35 U.S.C. 154(b) by 0 days.

(21) Appl. No.: 09/462,768
(22) PCT Filed: Jul. 15, 1998
(86) PCT No.: PCT/AT98/00173
§ 371 Date: Jan. 13, 2000
§ 102(e) Date: Jan. 13, 2000
(87) PCT Pub. No.: WO99/03474
PCT Pub. Date: Jan. 28, 1999

(30) Foreign Application Priority Data

Jul. 15, 1997 (AT) .................................................... 1206/97

(51) Int. Cl.⁷ .................................................... A61K 31/60
(52) U.S. Cl. ........................ 514/165; 514/160; 514/159
(58) Field of Search .............................. 514/165; 424/232

(56) References Cited

U.S. PATENT DOCUMENTS

| 3,316,150 | 4/1967 | Faeges . |
| 4,228,162 | 10/1980 | Luzzi et al. . |
| 5,723,453 | 3/1998 | Phykitt . |

FOREIGN PATENT DOCUMENTS

| 0 055 635 | 7/1982 | (EP) . |
| 2 258 865 | 8/1975 | (FR) . |
| 1 489 672 | 10/1977 | (GB) . |
| WO 92 07559 | 5/1992 | (WO) . |
| WO 93 20815 | 10/1993 | (WO) . |
| WO 97 27750 | 8/1997 | (WO) . |

OTHER PUBLICATIONS

Chemical Abstracts, vol. 105, No. 18, Nov. 3, 1986, abstract No. 158814, & CS 227 456 B, Valenta et al, Apr. 15, 1986.

*Primary Examiner*—William R. A. Jarvis
*Assistant Examiner*—Vickie Kim
(74) *Attorney, Agent, or Firm*—Nixon & Vanderhye

(57) ABSTRACT

In a method for producing stable acetylsalicylic acid solutions with pharmaceutically acceptable non-aqueous organic solvents such as, e.g., dimethylisosorbide, propylene glycol or diethylene glycol monoethyl ether, 0.005–2% by weight of a cyclic acid imide and/or 0.005–2% by weight of a sulfaminic acid as well as, preferably, 1–40% by weight, based on the weight of the solution, of a compound of the general formula

I

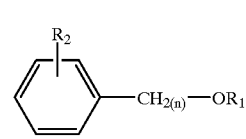

are added to the solution. In the general formula, $R_1$ represents H, $CH_3$ or $C_2H_5$, n=0 or 1, and $R_2$ represents H or one or more lower alkyl, lower alkyloxy or lower alkenyl residues having 1 to 5 carbon atoms.

15 Claims, No Drawings

METHOD FOR PRODUCING STABLE ACETYLSALICYLIC ACID SOLUTIONS

The invention relates to a method for producing stable acetylsalicylic acid solutions with pharmaceutically suitable non-aqueous organic solvents such as, e.g., dimethylisosorbide, propylene glycol or diethylene glycol monoethyl ether as well as stable solutions of acetylsalicylic acid and a preferred use of such solutions for the rapid dermal or sublingual absorption of the active substance.

The instability of acetylsalicylic acid in pharmaceutical preparations has already been known for long. The hydrolysis of acetylsalicylic acid in salicylic acid and acetic acid occurs relatively quickly as a function of a number of factors. Besides the known hydrolysis product salicylic acid, also acetylsalicylic anhydride and acetylsalicylosalicylic acid are known as impurities. The decomposition of aspirin results in a major loss of its pharmacological activity, in particular with the indication myocardial infarction prophylaxis, thus usually making acetylsalicylic acid be marketed only in the form of solid preparations. Solid preparations, in turn, as a rule can be administered only orally with rapid decomposition taking place primarily in the acidic environment of the stomach, during the absorption in the gastric mucuous membrane as well as through the first pass in the liver such that only approximately half of the acetylsalicylic acid will reach the blood stream in the decomposed form. The metabolite salicylic acid forming during absorption is made responsible for side effects such as, e.g., gastric hemorrhage and the overdosage required on account of the high degradation of the active substance during absorption constitutes a considerable additional burden on the organism.

In addition to the antiinflammatory, antipyretic and analgetic effects of aspirin, acetylsalicylic acid has been used also as an antirheumatic and for the prophylaxis of infarctions, wherein a number of tests have already been aimed to prevent the decomposition of the pharmaceutical preparation within the stomach in order to thereby avoid undesired side effects. It is advantageous, primarily in continuous therapy, to keep the concentration of salicylic acid in the organism as low as possible. For that reason, stable acetylsalicylic acid solutions have been developed, which upon dermal application are additionally able to transport the active substance rapidly into the skin and, further on, into the blood stream, so that a systemic action will take effect there without creating gastrointestinal side effects. Such solutions must exhibit a long-term stability for industrial exploitation.

The hydrolysis of aspirin to salicylic acid and acetic acid follows a kinetics of the first order and is catalyzed by both acids and bases. Due to the rapid hydrolysis of aspirin in aqueous media, attempts have so far been made to make liquid preparations of aspirin in non-aqueous solvents such as, e.g., propylene glycol, ethyl alcohol, glycerine or polyethylene glycol. Traces of moisture, deesterification or the like can, however, not be avoided with all those solvents such that only an insufficient stability will be obtained even in those cases. When using polyethylene glycol, deesterification into salicylic acid and acetylated polyethylene glycol has been observed upon extended storage. For that reason, esterified polyethylene glycols in liquid preparations have already been proposed.

A liquid preparation using dimethylisosorbide is to be taken from U.S. Pat. No. 4,228,162. Such a liquid solution may be characterized by a considerably enhanced stability as compared to a number of other solutions. Yet, even such solutions are not sufficiently stable for successful marketing and the long-term stability required. Moreover, dermal absorption proceeds only slowly upon application. The skin is wetted with liquid for a long time and it may, therefore, readily happen that the solution will be absorbed by clothes, thus preventing the active substance from being available for absorption by the body.

From EP 55 635 A1 a dermal preparation of acetylsalicylic acid has become known, which may be applied in the form of a gel. Dermal application, which sets particularly high demands on the stability of the solution, offers the advantage that the undesired first pass effect may be avoided and gastrointestinal irritations such as gastric hemorrhage do not occur. However, a prerequisite for an accordingly effective preparation is a high degree of stability, wherein EP 55 635 A1 inter alia proposes diethylene glycol monoethyl ether and propylene glycol. The preparation described there used a carboxyvinyl polymer for gel formation with ethylenediaminetetraacetic acid (EDTA) having been used for further stabilization.

Also that known preparation does not meet the required long-term stability and rapid absorption of the active substance. Departing from a solution of the initially defined kind, the present invention, therefore, aims to substantially enhance the stability and absorption of such solutions.

To solve this object, the method according to the invention for producing stable acetylsalicylic acid solutions with pharmaceutically safe non-aqueous organic solvents essentially consists in that 0.005–2% by weight of a cyclic acid imide and/or 0.005–2% by weight of a sulfaminic acid as well as, preferably, 1–40% by weight, based on the weight of the solution, of a compound of the general formula

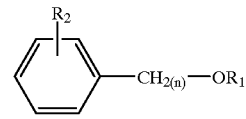

I wherein $R_1$ represents H, $CH_3$ or $C_2H_5$, n=0 or 1, and $R_2$ represents H or one or more lower alkyl, lower alkyloxy or lower alkenyl residues having 1 to 5 carbon atoms are added to the solution. The compounds of the general formula I indicated above frequently are components of essential oils or vegetable extracts. Thus, for instance, anise oil contains more than 90% anetholee, or fennel oil contains 50 to 60% anetholee, such that also these oils or extracts may be used depending on their concentrations of the compounds cited above.

Surprisingly, it has now been shown that the long-term stability of the solutions can be substantially enhanced by using the additives mentioned, wherein the admissible storage time could be raised by a factor of at least two. In doing so, it is essential to use the free acid rather than the Na salts as are found in sweetening agents, since the Na salts would destabilize the solutions. The range of concentration within which, for instance, saccharin may be used is at the lower limit of the concentrations used for stabilization, wherein it has been shown in a surprising manner that ethanol is not suitable as a solvent and ethanolic solutions of the active substance could not be stabilized with saccharin.

The highly fluid solutions are completely and irreversibly soaked into the skin within a few minutes without involving undesired external effects such as, e.g., clothes, distribution on other objects, and they are excellently suitable for dosing to precise acetylsalicylic acid contents by means of a dosing pump. Besides saccharin and/or cyclamic acid, compounds of the general formula I, to which anethole or benzyl alcohol belong in a preferred manner, have surprisingly proved to be of particular advantage. The exact mechanism by which long-term stability is substantially enhanced using the stabilizers proposed according to the invention could not be clarified for sure. The substitution of other organic acids such as sorbinic acid, benzoic acid or nicotinic acid for cyclamic acid or saccharin no longer resulted in an appropriate long-term stability. The values each determined in the long-term test in respect of the hydrolysis product salicylic acid formed over the time in any event were all far below half of the values observed with known solutions designated as stable.

Advantageously, the process according to the invention is carried out in a manner that cyclamic acid is used as said sulfamic acid. Like saccharin, which is preferably used as a cyclic acid imide, cyclamic acid in the concentrations mentioned has resulted in a storage quality at least twice as high.

The use of anethole and/or benzyl alcohol offers special advantages, in particular in dermal application, since with such additives used in the solution the skin will rapidly dry up again upon application and the active substance with the solvent will be extremely quickly absorbed, thus increasing the transcutaneous permeability for acetylsalicylic acid. In order to avoid degreasing of the skin upon application, the formulation may be supplemented with a slight amount of oleic acid. Oleic acid also may be replaced with other oils or greasing substances such as, e.g., vitamin E (acetate).

A particularly preferred stable solution of acetylsalicylic acid is characterized in that it contains 5–15% by weight acetylsalicylic acid, 10–40% by weight propylene glycol, 0–40% by weight dimethylisosorbide, 0–70% by weight diethylene glycol monoethylether and 0.005–2% by weight saccharin and/or cyclamic acid, and/or 1–40% by weight anethole, wherein the solution preferably contains 12.5% by weight acetylsalicylic acid and 30% by weight each of propylene glycol and dimethylisosorbide, which may both be replaced totally or partially with benzyl alcohol or anethole or a mixture of both said components, the balance-being diethylene glycol monoethyl ether as well as 0.1–0.5% by weight, based on the solution, of saccharin and/or cyclamic acid.

Another particularly preferred solution contains, in addition to acetylsalicylic acid, 20% by weight propylene glycol, 65% by weight diethylene glycol monoethyl ether and 0.1% by weight saccharin, cyclamic acid and/or 0.5 to 5% by weight anethole. Parts of diethylene glycol monoethyl ether may be replaced with benzyl alcohol or anethole or mixtures thereof, wherein 0.2 to 0.5% by weight cyclamic acid may preferably be used instead of saccharin.

Further enhancement of the stability of such solutions is, of course, feasible by storing the solutions under largely air- and moisture-tight conditions. The stable solution according to the invention in a particularly preferred manner, therefore, is present as an aerosol with a product seal ensuring that only that amount of air and hence moisture may accede in each case, which is required for displacing a predetermined dosable amount of the active substance in its solution, and enabling the precise proportioning of the active substance required for pharmaceutical purposes.

A particularly preferred stable solution is characterized in that it contains 10–24% by weight acetylsalicylic acid, 0.005–2% by weight saccharin and/or cyclamic acid, 20–80% by weight methoxy propanol, in particular 1-methoxy-2-propanol, and optionally 1–30% by weight benzyl alcohol and/or anethole as well as optionally propylene glycol and/or diethylene glycol monoethyl ether and optionally oleic acid and tocopherol (vitamin E). The use of 1-methoxy-2-propanol as a solvent allows for a substantially higher concentration of acetylsalicylic acid in the solution. What is essential in this respect, with a view to a rapid dermal absorption, is the amount dissolved and hence the concentration of acetylsalicylic acid in solution, wherein, when using 1-methoxy-2-propanol, elevated amounts of other solvents or solubilizers may be obviated and drying of the skin may be counteracted by the addition of oleic acid and optionally vitamin E.

Due to its high long-term stability, the stable solution according to the invention preferably is suitable for the pharmaceutical dermal or sublingual application, in particular also as an aerosol.

In the following, the invention will be explained in more detail by way of exemplary embodiments as compared to the prior art.

EXAMPLE 1

According to the prior art, 1 g acetylsalicylic acid was dissolved in 7 g diethylene glycol monoethyl ether (transcutol) and 2 g propylene glycol. The stability of the solution was followed by determining the hydrolysis product salicylic acid with an average formation of 0.076% by weight salicylic acid per day (storage at 25° C.) resulting. An absorption test carried out with the gel described in EP 55 635 A1 upon transdermal application showed relatively unfavorable values, since after 60 minutes only approximately half of the active substance applied was absorbed.

EXAMPLE 2

The solution according to Example 1 was supplemented with 0.005 g saccharin. The amount of the hydrolysis product salicylic acid formed over the time, which was determined in the same manner, revealed an average formation of 0.0377% by weight per day, from which resulted a duplication of the storage quality and an accordingly prolonged stability.

EXAMPLE 3

The solution according to Example 1 was supplemented with 0.01 g saccharin. The amount of salicylic acid formed per day on an average decreased to 0.031% by weight, from which resulted a further increase in the stability.

EXAMPLE 4

Departing from the solution according to Example 1, the amount of saccharin was increased to 0.05 g. The increase in the hydrolysis product averaged over the time showed a mean value of 0.025% by weight per day.

EXAMPLE 5

Departing from the solution according to Example 1, saccharin was added in an amount of 0.1 g. The amount of salicylic acid formed per day dropped to 0.0247% by weight.

EXAMPLE 6

For comparative purposes, a solution was prepared of 1 g acetylsalicylic acid, 3 g diethylene glycol monoethyl ether, 3 g dimethylisosorbide and 3 g propylene glycol. The formation of hydrolysis products determined over the time at a storage temperature of 25° C. was assessed at 0.046% by weight per day.

EXAMPLE 7

Departing from a solution according to Example 6, 0.02 g cyclamic acid was added. The average formation of salicylic acid dropped to a value of 0.024% by weight per day, from which a duplication of the stability resulted again.

EXAMPLE 8

Departing from a solution according to Example 6, 0.1 g cyclamic acid was added. The amount of salicylic acid formed per day increased to 0.032% by weight. Yet, this value was still significantly better than the value obtained without addition of cyclamic acid.

EXAMPLE 9

A stable solution was prepared of 1 g acetylsalicylic acid, 3 g dimethylisosorbide, 3 g diethylene glycol monoethyl ether, 3 g propylene glycol and 0.2 g saccharin. The amount of salicylic acid formed per day decreased to 0.0183% by weight, thus enabling the production of a particularly stable solution.

The absorption tests with dermal application revealed that more than half of the active substance applied was absorbed already after 30 minutes.

EXAMPLE 10

A stable solution was prepared of 1 g acetylsalicylic acid, 3 g benzyl alcohol, 3 g diethylene glycol monoethyl ether, 3 g propylene glycol and 0.05 g saccharin.

An absorption test was carried out with this solution, wherein more than half (57%) of the active substance was dermally absorbed within 15 minutes and nearly three fourths (73%) of the active substance were dermally absorbed within 30 minutes.

EXAMPLE 11

A stable solution was prepared of 1 g acetylsalicylic acid, 3 g anethole, 3 g diethylene glycol monoethyl ether, 3 g propylene glycol and 0.05 g saccharin.

The absorption tests with dermal application revealed an absorption of the active substance of 85% after 15 minutes and 93% after 30 minutes.

EXAMPLE 12

The following solutions were prepared:

| Amount of individual aerosol doses in mg | (A) mg | (B) mg | (C) mg | (D) mg | (E) mg |
|---|---|---|---|---|---|
| Acetylsalicylic acid ASS | 25.0 | 25.0 | 30.0 | 35.0 | 35.0 |
| Diethylene glycol monoethyl ether | 90.0 | — | 58.5 | 33.4 | 33.4 |
| 1-Methoxy-2-propanol | — | 90.0 | 58.5 | 103.6 | 133.6 |
| Anethole | 20.0 | 20.0 | 40.0 | 20.0 | — |
| Benzyl alcohol | 20.0 | 20.0 | 10.0 | 10.0 | — |
| Propylene glycol | 50.0 | 50.0 | 5.0 | 5.0 | 5.0 |
| Oleic acid | — | — | 2.0 | 2.0 | 2.0 |
| Saccharin | 1.0 | 1.0 | 1.0 | 1.0 | — |
|  | 205.1 | 205.1 | 204.1 | 210.0 | 210.0 |

In solution (B), diethylene glycol monoethyl ether was completely replaced with 1-methoxy-2-propanol. Under the same storage conditions, this solution showed a stability enhanced by a factor 1.75 as compared to solution (A).

Solution (C) was tested for its skin tolerance on man. No irritations were observed after a large-area application on man over a period of 1 month at a dosage of 150 mg.

Solution (D) constitutes a highly concentrated field-proven ASS solution, apportioning 35 mg ASS by one aerosol dose of 210 mg.

Approximately 48% was absorbed from formulations (D) and (E) after 10 minutes.

After 15 minutes, 63% was absorbed from solution (D) and 55% was absorbed from solution (E). That 55% absorption after 15 minutes is far higher than indicated in the literature for comparative solutions, corresponding to the absorption behavior of the solution prepared in Example 10 and containing compounds of the general formula (I).

Comparative tests with 0.01 g and 0.05 g benzoic acid yielded substantially higher values for the formation of salicylic acid as compared to the stabilizers according to the invention. Similar values were obtained with 0.05 g sorbic acid. The addition of 0.01 g nicotinic acid yielded poorer values than those corresponding to the prior art (0.74% by weight salicylic acid/day), the increase in the amount of nicotinic acid to 0.05 g resulting in a considerable deterioration of the stability (2.05% by weight salicylic acid/day).

Comparative absorption tests without any addition of the substances proposed according to the invention all showed poorer results. The solution in diemthylisosorbide according to U.S. Pat. No. 4,228,162 after 60 minutes led to an absorption of but 21% of the active substance. Even propylene glycol or transcutol as the sole solvents did not result in an absorption comparable to the values measured when using the additives according to the invention.

Anethole and benzyl alcohol, in addition to an enhanced absorption, also exhibited a significant stabilizing effect on the active substance and, therefore, may be employed as stabilizers together with saccharin or cyclamic acid as partial substitutes for the organic solvents.

What is claimed is:

1. A method for producing a stable acetylsalicylic acid solution comprising dissolving acetylsalicylic acid in a pharmaceutically acceptable non-aqueous organic solvent selected from the group consisting of dimethylisosorbide, propylene glycol and diethylene glycol monethyl ether, together with 0.05–2% by weight of a cyclic acid imide, or 0.05–2% by weight of a sulfaminic acid or both a cyclic acid imide and a sulfaminic acid and 1–40% by weight, based on the weight of the solution, of a compound of the formula:

(I)

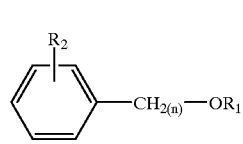

wherein $R_1$ represents H, $CH_3$ or $C_2H_5$, n=0 or 1, and $R_2$ represents H or a lower alkyl, lower alkyloxy or lower alkenyl group each having 1 to 5 carbon atoms.

2. The method according to claim 1, wherein cyclamic acid is used as said sulfaminic acid.

3. The method according to claim 1 or 2, wherein sulfonic acid imide or saccharin is used as said cyclic acid imide.

4. The method according to claim 1 or 2 wherein the compound of formula I is anethole or benzyl alcohol.

5. A stable solution of acetylsalicylic acid consisting essentially of:

5–15% by weight acetylsalicylic acid,

10–40% by weight propylene glycol,

0–40% by weight dimethylisosorbide,

0–70% by weight diethylene glycol monoethyl ether and, 0.05–2% by weight saccharin and/or cyclamic acid, and/or 1–40% by weight anethole and/or benzyl alcohol.

6. A stable solution consisting essentially of:

12.5% by weight acetylsalicylic acid,

30% by weight each of propylene glycol and dimethylisosorbide, or both the propylene glycol and dimethyl isosorbide are replaced totally or partially with benzyl alcohol or anethole or a mixture thereof, the balance being diethylene glycol monoethyl ether and 0.1–0.5% by weight, based on the weight of the solution, of saccharin and/or cyclamic acid.

7. The stable solution according to claim 5 or 6, wherein the solution contains 20% by weight propylene glycol, 65% by weight diethylene glycol monoethyl ether and 0.1% by weight saccharin and/or cyclamic acid and/or 0.5 to 5% by weight anethole.

8. The stable solution according to claim 5 or 6 present as an aerosol.

9. A stable solution consisting essentially of:

10–24% by weight acetylsalicylic acid, 0.05–2% by weight saccharin and/or cyclamic acid, 20–80% by weight methoxy propanol, and optionally: 1–30% by weight benzyl alcohol and/or anethole, propylene glycol, diethylene glycol monoethyl ether, oleic acid, tocopherol or mixtures thereof.

10. A method of administering acetylsalicylic acid to a patient comprising dermally or sublingually administering to said patient a stable solution of acetylsalicylic acid consisting essentially of 5–15% by weight acetylsalicylic acid, 10–40% by weight propylene glycol, 0–40% by weight dimethylisosorbide, 0–70% by weight diethylene glycol monoethyl ether and, 0.05–2% by weight saccharin and/or cyclamic acid, and/or 1–40% by weight anethole and/or benzyl alcohol.

11. A method of administering acetylsalicylic acid to a patient comprising dermally or sublingually administering to said patient a stable solution of 12.5% by weight acetylsalicylic acid, 30% by weight each of propylene glycol and dimethylisosorbide, or both the propylene glycol and dimethyl isosorbide are replaced totally or partially with benzyl alcohol or anethole or a mixture thereof, the balance being diethylene glycol monoethyl ether and 0.1–0.5% by weight, based on the weight of the solution, of saccharin and/or cyclamic acid.

12. In a method for producing a stable acetylsalicylic acid solution with pharmaceutically acceptable non-aqueous organic solvents selected from dimethylisosorbide, propylene glycol or diethylene glycol monoethyl ether, the improvement comprising adding to the solution 0.05–2% by weight of a cyclic acid imide or 0.05–2% by weight of a sulfaminic acid or both a cyclic acid and a sulfaminic acid and 1–40% by weight, based on the weight of the solution, of a compound of the formula

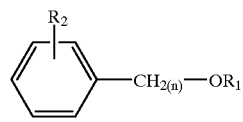

(I)

wherein $R_1$ represents H, $CH_3$ or $C_2H_5$, n=0 or 1, and $R_2$ represents H or one or a lower alkyl, lower alkyloxy or lower alkenyl group each having 1 to 5 carbon atoms.

13. The method according to claim 12, wherein the cyclamic acid is used as said sulfaminic acid.

14. The method according to claim 12 or 13, wherein sulfonic acid imide or saccharin is used as said cyclic acid imide.

15. The method according to claim 12, wherein the compound of formula I anethole or benzyl alcohol are used as said compound of the general formula I.

* * * * *